United States Patent
Oda et al.

(10) Patent No.: US 9,233,081 B2
(45) Date of Patent: Jan. 12, 2016

(54) FAT-REDUCING AGENT

(71) Applicant: FUJIFILM Corporation, Minato-ku, Tokyo (JP)

(72) Inventors: Yuriko Oda, Kanagawa (JP); Fumitaka Ueda, Kanagawa (JP); Shinichiro Serizawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/779,225

(22) Filed: Feb. 27, 2013

(65) Prior Publication Data

US 2013/0172426 A1    Jul. 4, 2013

Related U.S. Application Data

(63) Continuation of application No. PCT/JP2012/057070, filed on Mar. 19, 2012.

(30) Foreign Application Priority Data

Mar. 29, 2011   (JP) .................................. 2011-072918

(51) Int. Cl.
| | |
|---|---|
| *A61K 31/01* | (2006.01) |
| *A23L 1/30* | (2006.01) |
| *A23L 1/275* | (2006.01) |
| *A61K 9/107* | (2006.01) |
| *A61K 9/14* | (2006.01) |

(52) U.S. Cl.
CPC ............... *A61K 31/01* (2013.01); *A23L 1/2751* (2013.01); *A23L 1/30* (2013.01); *A23L 1/3008* (2013.01); *A61K 9/107* (2013.01); *A61K 9/146* (2013.01); *A23V 2002/00* (2013.01)

(58) Field of Classification Search
CPC ............... A23V 2002/00; A23V 2200/3322; A23V 2250/211; A23L 1/2751; A23L 1/30; A23L 1/3008; A61K 31/01; A61K 9/107; A61K 9/146
See application file for complete search history.

(56) References Cited

U.S. PATENT DOCUMENTS

| 6,903,134 B2 * | 6/2005 | Pflucker et al. ............... 514/470 |
|---|---|---|
| 2007/0190080 A1 | 8/2007 | Friedman |
| 2010/0055191 A1 * | 3/2010 | Arakawa et al. .............. 424/489 |

FOREIGN PATENT DOCUMENTS

| EP | 1 864 578 A1 | 12/2007 |
|---|---|---|
| EP | 2 380 552 A1 | 10/2011 |
| EP | 2 676 553 A1 | 12/2013 |
| EP | 2 767 274 A1 | 8/2014 |
| EP | 2 829 263 A1 | 1/2015 |
| JP | 2007-517859 A | 7/2007 |
| JP | 2007-269631 A | 10/2007 |
| JP | 2008-63476 A | 3/2008 |
| JP | 2008-231057 A | 10/2008 |
| JP | 2009-114184 A | 5/2009 |
| JP | 2009-535303 A | 10/2009 |
| JP | 2010-168285 A | 8/2010 |
| JP | 2010-270021 A | 12/2010 |
| JP | 2011-241177 A | 12/2011 |
| WO | 2010/084789 A1 | 7/2010 |
| WO | 2011/145659 A1 | 11/2011 |

OTHER PUBLICATIONS

JP 2007-26931, machine translation.*
Written Opinion (10 pages) for PCT/JP2012/057070 dated May 1, 2012.
International Search Report for PCT/JP2012/057070 dated May 1, 2012.
Office Action dated May 20, 2014 issued by the Japanese Patent Office in Japanese Patent Application No. 2011-072918.
Extended European Search Report dated May 29, 2015 from the European Patent Office in counterpart EP Application No. 12765228.7.
Office Action dated May 20, 2015 from the State Intellectual Property Office of the People's Republic of China in counterpart CN Application No. 201280003010.X.
Office Action dated Sep. 10, 2014, issued by the State Intellectual Property Office of People's Republic of China in corresponding Chinese Application No. 201280003010.X.

* cited by examiner

*Primary Examiner* — Savitha Rao
(74) *Attorney, Agent, or Firm* — Sughrue Mion, PLLC

(57) ABSTRACT

A fat-reducing agent includes a carotenoid-containing composition as an active ingredient, the carotenoid-containing composition including: a carotenoid component including at least one crystalline carotenoid, wherein at least 90% by mass of the crystalline carotenoid is in the non-crystalline state; and a (poly)glycerin fatty acid ester containing from 1 to 6 glycerin units and from 1 to 6 fatty acid units, and having at least one hydroxyl group in the glycerin units.

11 Claims, No Drawings

FAT-REDUCING AGENT

CROSS-REFERENCE TO RELATED APPLICATIONS

This application is a continuation application of International Application No. PCT/JP/2012/057070, filed Mar. 19, 2012, which is incorporated herein by reference. Further, this application claims priority from Japanese Patent Application No. 2011-072918, filed Mar. 29, 2011, which is incorporated herein by reference.

TECHNICAL FIELD

The present invention relates to a fat-reducing agent.

BACKGROUND ART

Since neutral fat accumulated in the body owing to lack of exercise, excessive eating, etc. increases the risk of life-style related diseases, there has recently been a desire for suppression of the accumulation of neutral fat. Further, various compositions containing carotenoid have been developed, focusing on high functionality of carotenoid. In such a circumstance, various techniques have been proposed, expecting that carotenoid exerts fat accumulation suppressing effects.

For example, Japanese Patent National-Stage Publication (JP-A) No. 2009-535303 proposes use of a lycopene compound in treatment of metabolic function disorder, and discloses that the total cholesterol and triglyceride concentrations in blood serum are normalized using, for example, a lactolycopene formulation.

Furthermore, Japanese Patent Application Laid-Open (JP-A) No. 2007-269631 discloses that lycopene extracted from tomato oleoresin decreases neutral fat concentrations in liver and in blood.

SUMMARY OF INVENTION

Technical Problem

However, crystalline carotenoid such as lycopene has high crystallinity, and crystals may often remain when a composition containing a crystalline carotenoid is prepared. Thus, there are cases in which compositions containing crystals do not provide expected effects because of the presence of the crystals. Furthermore, in an example in which the lycopene is used for suppressing accumulation of neutral fat, the resultant effect in terms of suppression of the accumulation is not as high as expected.

Accordingly, an object of the present invention is to provide a fat-reducing agent which contains a crystalline carotenoid and which exerts a strong effect in terms of reducing the accumulation amount of fat.

Solution to Problem

Aspects of the invention include the following.

[1] A fat-reducing agent including a carotenoid-containing composition as an active ingredient, the carotenoid-containing composition containing:

a carotenoid component including at least one crystalline carotenoid, wherein at least 90% by mass of the crystalline carotenoid is non-crystal; and a (poly)glycerin fatty acid ester containing from 1 to 6 glycerin units and from 1 to 6 fatty acid units, and having at least one hydroxyl group in the glycerin units.

[2] The fat-reducing agent according to [1], wherein the crystalline carotenoid is lycopene.

[3] The fat-reducing agent according to [1] or [2], wherein the (poly)glycerin fatty acid ester has a molecular weight of 10,000 or less.

[4] The fat-reducing agent according to any one of [1] to [3], wherein each fatty acid component of the fatty acid units of the (poly)glycerin fatty acid ester is a fatty acid having from 8 to 22 carbon atoms.

[5] The fat-reducing agent according to any one of [1] to [4], wherein the total mass of the (poly)glycerin fatty acid ester is from 0.01 times to 10 times the total mass of the crystalline carotenoid.

[6] The fat-reducing agent according to any one of [1] to [5], further including an antioxidant.

[7] The fat-reducing agent according to [6], wherein the antioxidant includes at least one selected from the group consisting of ascorbic acid, an ascorbic acid ester and a salt thereof, in a molar quantity that is from 0.01 times to 10 times the molar quantity of the carotenoid component.

[8] The fat-reducing agent according to any one of [1] to [7], further including an emulsifying agent.

[9] The fat-reducing agent according to [8], wherein the emulsifying agent includes a nonionic surfactant selected from the group consisting of a sucrose fatty acid ester, a polyglycerin fatty acid ester, an organic acid monoglyceride, a propylene glycol fatty acid ester, a polyglycerin-condensed ricinoleic acid ester, a sorbitan fatty acid ester and a polyoxyethylene sorbitan fatty acid ester.

[10] The fat-reducing agent according to [8] or [9], wherein the carotenoid-containing composition is an oil-in-water composition in which an oil phase composition containing the carotenoid component and the (poly)glycerin fatty acid ester is dispersed in a water phase composition containing water and the emulsifying agent.

[11] The fat-reducing agent according to [8] or [9], wherein the carotenoid-containing composition is a powder composition obtained by drying an oil-in-water composition in which an oil phase composition containing the carotenoid component and the (poly)glycerin fatty acid ester is dispersed in a water phase composition containing water and the emulsifying agent.

[12] A method of producing the fat-reducing agent according to any one of [1] to [11], the method including:

preparing an oil phase component mixture liquid containing the carotenoid component and the (poly)glycerin fatty acid ester; and heating the oil phase component mixture liquid at a temperature equal to or higher than the melting temperature of the carotenoid component.

[13] The production method according to [12], wherein the highest temperature during the heating is higher than the melting temperature of the carotenoid component by no more than 10° C.

[14] The fat-reducing agent production method according to [12] or [13], further including pressure-emulsifying an oil phase composition obtained by the heating and a water phase composition containing an emulsifying agent, to obtain an oil-in-water emulsion composition.

[15] Use of a carotenoid-containing composition for production of a fat-reducing agent, the carotenoid-containing composition including:

a carotenoid component including at least one crystalline carotenoid, wherein at least 90% by mass of the crystalline carotenoid is non-crystal; and a (poly)glycerin fatty acid ester containing from 1 to 6 glycerin units and from 1 to 6 fatty acid units, and having at least one hydroxyl group in the glycerin units.

[16] A method of preventing or treating a symptom or disease accompanied by fat accumulation, the method including administering the fat-reducing agent according to any one of [1] to [11] to a subject that exhibits a symptom potentially involving an increase in fat accumulation amount or to a subject with a disease potentially involving an increase in fat accumulation amount.

[17] A food including the fat-reducing agent according to any one of [1] to [11].

Advantageous Effects of Invention

According to the present invention, a fat-reducing agent can be provided which contains a crystalline carotenoid and which has a strong effect in terms of reducing the accumulation amount of fat.

BEST MODE FOR CARRYING OUT THE INVENTION

The fat-reducing agent of the present invention is a fat-reducing agent that includes a carotenoid-containing composition as an active ingredient, the carotenoid-containing composition containing: a carotenoid component which includes at least one crystalline carotenoid, and in which at least 90% by mass of the crystalline carotenoid is in the non-crystalline state; and a (poly)glycerin fatty acid ester that contains from 1 to 6 glycerin units and from 1 to 6 fatty acid units, and that has at least one hydroxyl group in the glycerin units.

According to the invention, since the carotenoid-containing composition in the fat-reducing agent contains the specified (poly)glycerin fatty acid ester and a crystalline carotenoid which is mainly in the non-crystalline state, a stronger effect with respect to reduction in fat accumulation amount can be obtained as compared to a case in which a crystalline carotenoid in the highly-crystalline state, such as the state of, for example, having been extracted from natural products, is contained. In other words, the fat-reducing agent of the invention can reduce fats such as neutral fat, subcutaneous fat and visceral fat, and in particular, can reduce neutral fat. Furthermore, the fat-reducing agent of the invention can reduce the amount of fats in the body, and can reduce the body weight.

In the present specification, any numerical range expressed using "to" refers to a range that includes the numerical values described before and after "to" as the minimum value and the maximum value, respectively.

In a case in which the amount of a component that may be included in the composition is indicated in the invention, when there are plural substances corresponding to the component in the composition, the indicated amount means the total amount of the plural substances present in the composition, unless specifically stated otherwise.

The scope of the term "process" as used herein includes not only a discrete process, but also a process that cannot be clearly distinguished from another process as long as the expected effect of the process of interest is achieved.

In the invention, "fat reduction" means a reduction in the accumulation amount of fat, and means that, after the use (intake) of the fat-reducing agent, the amount of fat accumulated in the body, such as in the blood, under the skin or in internal organs, is reduced, or an increase in fat accumulation amount due to accumulation of accumulable fat is suppressed, as compared with those before the use (administration) of the fat-reducing agent.

In the specification, the expression "(poly)glycerin fatty acid ester" encompasses a glycerin fatty acid ester that contains one glycerin unit and one fatty acid unit, a glycerin fatty acid ester that contains plural glycerin units and one fatty acid unit or contains one glycerin unit and plural fatty acid units, and a glycerin fatty acid ester that contains plural glycerin units and plural fatty acid units; this expression is used when these glycerin fatty acid esters are collectively referred.

Hereinbelow, the invention will be explained.

<Fat-Reducing Agent>

(Carotenoid-Containing Composition)

The fat-reducing agent of the invention contains a carotenoid-containing composition as an active ingredient, the carotenoid-containing composition including: a carotenoid component which includes at least one crystalline carotenoid, and in which at least 90% by mass of the crystalline carotenoid is in the non-crystalline state; and a (poly)glycerin fatty acid ester including from 1 to 6 glycerin units and from 1 to 6 fatty acid units, and having at least one hydroxyl group in the glycerin units. The carotenoid-containing composition may be in any form, and may be an oil phase composition composed only of components capable of forming an oil phase (hereinafter sometimes simply referred to as "oil phase component"), or an oil-in-water emulsion composition obtained by mixing and emulsifying, using an emulsifying agent, the oil phase composition and a water phase composition composed of specified water-soluble components capable of forming a water phase (hereinafter sometimes simply referred to as "water phase component"). From the viewpoint of systemic absorption, the carotenoid-containing composition is preferably an emulsion composition.

The carotenoid-containing composition of the invention can be used for fat reduction. Therefore, embodiments of the invention also include the following.

[1] A carotenoid-containing composition for reducing fat, including:

a carotenoid component that includes at least one crystalline carotenoid, wherein at least 90% by mass of the crystalline carotenoid is in a non-crystalline state;

a (poly)glycerin fatty acid ester containing from 1 to 6 glycerin units and from 1 to 6 fatty acid units, and having at least one hydroxyl group in the glycerin units.

[2] The carotenoid-containing composition for reducing fat according to [1], wherein the crystalline carotenoid is lycopene.

[3] The carotenoid-containing composition for reducing fat according to [1] or [2], wherein the (poly)glycerin fatty acid ester has a molecular weight of 10,000 or less.

[4] The carotenoid-containing composition for reducing fat according to any one of [1] to [3], wherein each fatty acid component of the fatty acid units of the (poly)glycerin fatty acid ester is a fatty acid having from 8 to 22 carbon atoms.

[5] The carotenoid-containing composition for reducing fat according to any one of [1] to [4], wherein the total mass of the (poly)glycerin fatty acid ester is from 0.01 to 10 times the total mass of the crystalline carotenoid.

[6] The carotenoid-containing composition for reducing fat according to any one of [1] to [5], further including an anti-oxidant.

[7] The carotenoid-containing composition for reducing fat according to [6], wherein the anti-oxidant includes at least one selected from the group consisting of ascorbic acid, an ascorbic acid ester and a salt thereof, in a molar amount that is from 0.01 to 10 times the molar amount of the carotenoid component.

[8] The carotenoid-containing composition for reducing fat according to any one of [1] to [7], further including an emulsifying agent.

[9] The carotenoid-containing composition for reducing fat according to [8], wherein the emulsifying agent includes a nonionic surfactant selected from the group consisting of a sucrose fatty acid ester, a polyglycerin fatty acid ester, an organic acid monoglyceride, a propylene glycol fatty acid ester, a polyglycerin-condensed ricinoleic acid ester, a sorbitan fatty acid ester and a polyoxyethylene sorbitan fatty acid ester.

[10] The carotenoid-containing composition for reducing fat according to [8] or [9], wherein the carotenoid-containing composition is an oil-in-water composition in which an oil phase composition containing the carotenoid component and the (poly)glycerin fatty acid ester is dispersed in a water phase composition containing water and the emulsifying agent.

[11] The carotenoid-containing composition for reducing fat according to [8] or [9], wherein the carotenoid-containing composition is a powder composition obtained by drying an oil-in-water composition in which an oil phase composition containing the carotenoid component and the (poly)glycerin fatty acid ester is dispersed in a water phase composition containing water and the emulsifying agent.

[12] A method of producing the carotenoid-containing composition for reducing fat according to any one of [1] to [11], the method including:
preparing an oil phase component mixture liquid containing the carotenoid component and the (poly)glycerin fatty acid ester; and
heating the oil phase component mixture liquid at a temperature equal to or higher than the melting temperature of the carotenoid component.

[13] The production method according to [12], wherein the highest temperature during the heating is higher than the melting temperature of the carotenoid component by no more than 10° C.

[14] The method of producing the carotenoid-containing composition for reducing fat according to [12] or [13], further including pressure-emulsifying an oil phase composition obtained by the heating and a water phase composition containing an emulsifying agent, to obtain an oil-in-water emulsion composition.

[15] Use of the carotenoid-containing composition for reducing fat according to any one of [1] to [11], for production of a fat-reducing agent.

[16] A method of producing a pharmaceutical agent for reducing fat, the method using the carotenoid-containing composition for reducing fat according to any one of [1] to [11].

[17] A method of preventing or treating a symptom or disease state accompanied by fat accumulation, the method including administering the carotenoid-containing composition for reducing fat according to any one of [1] to [11] to a subject that exhibits a symptom potentially involving an increase in fat accumulation amount or to a subject with a disease potentially involving an increase in fat accumulation amount.

[18] A food including the carotenoid-containing composition for reducing fat according to any one of [1] to [11].

[Carotenoid Component]

The carotenoid component in the carotenoid-containing composition of the invention includes at least one crystalline carotenoid, and at least 90% by mass of the crystalline carotenoid is present in the non-crystalline state in the carotenoid-containing composition.

Since the crystalline carotenoid contained in the carotenoid component is in the non-crystalline state, an effect with respect to reduction of fat accumulation amount can favorably be exerted.

Whether or not the crystalline carotenoid is in the non-crystalline state can be confirmed by known means for crystal structure detection, such as by using differential scanning calorimetry (DSC), polarization microscopic observation, X-ray diffraction, etc. The crystalline carotenoid can be judged as being in the non-crystalline state if no crystal is detected by these known techniques. In particular, in the invention, the non-crystalline state is preferably confirmed based on the presence of a DSC endothermic peak. Specifically, using a DSC Q2000 (TA Instruments Japan), one temperature increase-decrease (15° C./min) cycle is carried out over a temperature range of from 30° C. to 200° C., and endothermic and exothermic temperatures are determined. Here, in the case of an emulsion, the measurement is carried out after the emulsion is freeze-dried for water removal, and, in the case of a powder composition, the measurement is carried out in the powder state. If the presence of a recognizable endothermic peak is not observed, the carotenoid is judged as being in the non-crystalline state.

In the carotenoid component, at least from 90 to 100% by mass of the crystalline carotenoid should be in the non-crystalline state, and it is preferable that from 95 to 100% by mass of the crystalline carotenoid is in the non-crystalline state from the viewpoint of dynamic absorption. For example, whether at least 90% by mass of the crystalline carotenoid contained in the carotenoid component is in the non-crystalline state or not can be confirmed by comparison between the endothermic energy amount of the endothermic peak derived from the carotenoid crystals in the composition of the invention measured by differential scanning calorimetry (DSC), and the endothermic energy amount of the endothermic peak of a carotenoid crystal standard sample. In the invention, this method using DSC is used for confirming whether the crystalline carotenoid is in the non-crystalline state or not.

A case in which less than 90% by mass of the crystalline carotenoid is in the non-crystalline state is not preferable since, for example, a large amount of crystals occur in the case of preparing the carotenoid-containing composition in the form of an emulsion. Whether at least 90% by mass of the crystalline carotenoid contained in the carotenoid component is in the non-crystalline state or not can also be confirmed by comparison between the X-ray diffraction spectrum of the composition of the invention and the X-ray diffraction spectrum of a carotenoid crystal standard sample.

The content ratio of crystalline carotenoid in the non-crystalline state can be obtained by calculation from a DSC peak area or from the result of X-ray diffraction (XRD), also using a carotenoid agent that is a crystal available as a commercial product of which the content ratio of crystalline carotenoid in the crystal state is regarded as 100%. Examples of commercial products of carotenoid agents in the crystal state include biochemical agents available from Wako Pure Chemical Industries Ltd.

The "crystalline carotenoid" in the invention is not limited to particular types of carotenoid, and means a carotenoid which is capable of being present as a crystal at some temperature within a range of from −5° C. to 35° C. depending on various factors such as its production method, treatment, or storage, in a case in which the crystalline carotenoid is made into the form of a carotenoid-containing oil, paste or the like.

The presence of the crystal may be confirmed by general methods, and may be confirmed by, for example, differential scanning calorimetry (DSC), polarization microscopic observation or X-ray diffraction.

Crystalline carotenoids are colorants of yellow to red terpenoids, and examples thereof include those derived from plants, alga and bacteria. Crystalline carotenoids are not limited to naturally-derived carotenoids, and any crystalline carotenoid that can be obtained according to a general method may be employed. General methods may be employed to confirm whether a carotenoid is a crystalline carotenoid or not; for example, differential scanning calorimetry (DSC), polarization microscopic observation, X-ray diffraction, etc. may be used.

Specific examples of the crystalline carotenoid in the invention include lycopene, α-carotene, β-carotene, γ-carotene, β-carotene, actinioerythrose, bixin, canthaxanthin, capsorubin, β-8'-apo-carotenal (apocarotenal), β-12'-apo-carotenal, xanthophylls (such as astaxanthin, fucoxanthin, rutein, zeaxanthin, capsanthin, β-cryptoxanthin and violaxanthin) and fucoxanthin, and hydroxyl or carboxyl derivatives thereof. These may be used singly, or in combination of two or more thereof.

Lycopene and fucoxanthin are preferable as crystalline carotenoids, and they may be used singly or in combination.

In particular, the crystalline carotenoid is preferably lycopene from the viewpoint of an effect in terms of reducing the accumulation amount of fat.

Lycopene is a carotenoid having a chemical formula, $C_{40}H_{56}$ (molecular weight: 536.87), and belongs to a carotene group, which is a type of carotenoids. Lycopene is a red colorant having an absorption maximum at 474 nm (in acetone).

Lycopene has cis- and trans-isomers with respect to the conjugate double bond at the center of its molecule. Examples thereof include an all-trans isomer, a 9-cis-isomer, a 13-cis-isomer, etc., any of which may be used in the invention.

The carotenoid-containing composition may include lycopene in the form of a lycopene-containing oil or paste obtained by separation/extraction from a lycopene-containing natural product.

Lycopene is contained in tomato, persimmon, watermelon and pink grapefruit in nature, and the lycopene-containing oil may be one that has been separated/extracted from such a natural product.

The lycopene used in the invention may be an extract obtained by extraction from the natural products, or a product obtained by appropriately purifying the extract in accordance with the necessity, or a synthetic product.

In the invention, lycopene extracted from tomato is particularly preferable from the viewpoints of quality and productivity.

In the invention, widely-sold tomato extracts may be used lycopene-containing oils or pastes. Examples of the lycopene-containing oils or pastes include Lyc-O-Mato 15% and Lyc-O-Mato 6% (available from Sunbright Co., Ltd.) and LYCOPENE 18 (available from Kyowa Hakko Kogyo Co., Ltd.).

The carotenoid component may include only the crystalline carotenoid, or may be composed of the crystalline carotenoid as well as an oil content (oil) used for extraction from a natural product.

The content of crystalline carotenoid in the carotenoid-containing composition is preferably from 0.1% by mass to 5% by mass, more preferably from 0.2% by mass to 4% by mass, and further more preferably from 0.3% by mass to 3% by mass, with respect to the total mass of the solids (all components except water) contained in the carotenoid-containing composition. When the content is within the above range, it is expected that the effect in terms of reducing the accumulation amount of fat can be further heightened.

The carotenoid component may include, in addition to the crystalline carotenoid, a naturally-derived non-crystalline carotenoid (non-crystalline carotenoid).

[(Poly)glycerin Fatty Acid Ester]

The (poly)glycerin fatty acid ester in the carotenoid-containing composition is a (poly)glycerin fatty acid ester containing from 1 to 6 glycerin units and from 1 to 6 fatty acid units, and having at least one hydroxyl group in the glycerin units.

This specific (poly)glycerin fatty acid ester has high compatibility with crystalline carotenoid, and decreases the melting temperature of the crystalline carotenoid. In a product in which the (poly)glycerin fatty acid ester and the crystalline carotenoid are dissolved together, re-crystallization of the crystalline carotenoid is suppressed. As a result, a favorable effect in terms of reducing the accumulation amount of fat can be attained.

(Poly)glycerin fatty acid esters containing 7 or more glycerin units have high hydrophilicity, and, therefore, their compatibility with carotenoids is low. On the other hand, (poly) glycerin fatty acid esters containing 7 or more fatty acid units are not considered to produce an effect in terms of suppressing crystallization of carotenoids. Furthermore, (poly)glycerin fatty acid esters that do not have any hydroxyl group in the glycerin unit, such as medium-chain fatty acid triglycerides, cannot sufficiently suppress the crystallization of carotenoids. Therefore, it is thought that the effect in terms of suppressing the crystallization of carotenoids is not produced without a certain amount of hydroxyl groups.

From the viewpoints of, for example, suppressing re-crystallization, it is preferable that the (poly)glycerin fatty acid ester is an ester of a (poly)glycerin in which the number of glycerin units (average polymerization degree) is from 1 to 6, more preferably from 1 to 4, and a fatty acid having from 8 to 22 carbon atoms (such as caprylic acid, capric acid, lauric acid, myristic acid, palmitic acid, stearic acid, oleic acid, linoleic acid or behenic acid), more preferably a fatty acid having from 14 to 18 carbon atoms, wherein, in the ester, from 1 to 6 (more preferably from 1 to 5) fatty acid units each formed from a fatty acid as mentioned above are present.

From the viewpoints of uniform dissolution at the time of co-dissolution, the (poly)glycerin fatty acid ester preferably has a molecular weight of 10,000 or less, more preferably 3,000 or less, and further more preferably 2,500 or less. From the viewpoint of compatibility with carotenoids, the (poly) glycerin fatty acid ester preferably has a HLB of 9 or less, and more preferably 6 or less.

In a case in which the carotenoid-containing composition is in the form of a powder composition obtained by drying an emulsion composition, the (poly)glycerin fatty acid ester is preferably solid at normal temperature from the viewpoints of the carotenoid concentration in the carotenoid powder composition and the yield at the time of hot-air drying during the production of the composition. Specifically, in a case in which the (poly)glycerin fatty acid ester is solid at normal temperature, there is no need for increase in the amount of an encapsulating agent, as a result of which sufficient amount of carotenoid can be contained in the carotenoid-containing composition. Furthermore, in the case in which the (poly) glycerin fatty acid ester is solid at normal temperature, the (poly)glycerin fatty acid ester is less likely to adhere to a contact surface at the time of hot-air drying, as a result of which a decrease in the yield of the carotenoid powder composition can be suppressed. The (poly)glycerin fatty acid ester that is solid at normal temperature may be a (poly)glycerin fatty acid ester in which fatty acids for forming the fatty acid units do not have a branched chain or an unsaturated bond. Examples thereof include glyceryl myristate, glyceryl monostearate, glyceryl distearate, diglyceryl monostearate, tetraglyceryl monostearate, tetraglyceryl tristearate, tetraglyceryl pentastearate, hexaglyceryl monostearate, hexaglyceryl tristearate, hexaglyceryl tetrabehenate and hexaglyceryl pentastearate.

Examples of (poly)glycerin fatty acid esters that can be used in the carotenoid-containing composition include glyceryl myristate, monoglyceryl monostearate, diglyceryl monostearate, triglyceryl monostearate, hexaglyceryl pentastearate, triglyceryl dipalmitate, glyceryl distearate, tetraglyceryl tristearate, tetraglyceryl pentastearate, hexaglyceryl monostearate, hexaglyceryl tristearate and hexaglyceryl tetrabehenate. From the viewpoint of suppression of re-crystallization and the viewpoint of uniform dissolution property, glyceryl myristate, glyceryl monostearate, diglyceryl monostearate, tetraglyceryl pentastearate and hexaglyceryl pentastearate are preferable.

The (poly)glycerin fatty acid esters that can be used in the carotenoid-containing composition may be used singly, or in combination of two or more thereof.

A preferable content (mass) of the (poly)glycerin fatty acid ester may vary with the type or content of the crystalline carotenoid employed. From the viewpoint of the stability of the carotenoid-containing composition, the content of the (poly)glycerin fatty acid ester is preferably from 0.01 times to 10 times the total mass of the crystalline carotenoid, more preferably from 0.1 times to 8 times the total mass of the crystalline carotenoid, and still more preferably from 0.3 times to 5 times the total mass of the crystalline carotenoid. When the total mass of the polyglycerin fatty acid ester in the carotenoid-containing composition is not less than 0.01 times the total mass of the crystalline carotenoid, a sufficient effect in terms of suppressing crystallization may be obtained. When the total mass of the polyglycerin fatty acid ester in the carotenoid-containing composition is not more than 10 times the total mass of the crystalline carotenoid, an increase in particle diameters of dispersed particles (emulsified particles) when an emulsion is produced can be suppressed.

[Antioxidant]

The carotenoid-containing composition preferably contains an antioxidant.

Examples of the antioxidant include ascorbic acid compounds. Examples of ascorbic acid compounds include at least one selected from the group consisting of ascorbic acid, an ascorbic acid ester and a salt thereof (hereinafter sometimes referred to as "ascorbic acid-type antioxidant"). It is presumed that the ascorbic acid-type antioxidant acts as a protective agent for the carotenoid component during high temperature treatment. Use of the antioxidant reliably suppresses decomposition (such as oxidative decomposition) of the carotenoid component caused by heating, and suppresses a decrease in carotenoid component during the process of producing a carotenoid-containing composition.

Examples of the ascorbic acid-type antioxidant include L-ascorbic acid, sodium L-ascorbate, potassium L-ascorbate, calcium L-ascorbate, L-ascorbyl phosphate, magnesium L-ascorbyl phosphate, L-ascorbyl sulfate, disodium L-ascorbyl sulfate, L-ascorbyl stearate, L-ascorbic acid 2-glucoside, L-ascorbyl palmitate and L-ascorbyl tetraisopalmitate; and fatty acid esters of ascorbic acid such as L-ascorbyl stearate, L-ascorbyl tetraisopalmitate and L-ascorbyl palmitate. Of these, from the viewpoint of suppression of loss of carotenoid due to heat, L-ascorbic acid, sodium L-ascorbate, calcium L-ascorbate, L-ascorbyl stearate, L-ascorbic acid 2-glucodise, L-ascorbyl palmitate, magnesium L-ascorbyl phosphate, disodium L-ascorbyl sulfate and L-ascorbyl tetraisopalmitate are particularly preferable.

The ascorbic acid-type antioxidant as it is may be contained in the carotenoid-containing composition as an oil phase composition, or the ascorbic acid-type antioxidant may be contained in the form of an aqueous solution in the carotenoid-containing composition as an oil phase composition. The concentration of ascorbic acid-type antioxidant in the aqueous solution is not particularly limited, and is preferably from 0.05% by mass to 5% by mass with respect to the total mass of the carotenoid-containing composition, from the viewpoint of suppression of oxidation.

From the viewpoint of suppressing the loss of carotenoid component caused by heat, the total content of ascorbic acid-type antioxidant in the carotenoid-containing composition is preferably a molar quantity that is from 0.01 times to 10.0 times the molar quantity of the carotenoid component, more preferably from 0.1 times to 8.0 times the molar quantity of the carotenoid component, and further more preferably from 1.0 times to 6.5 times the molar quantity of the carotenoid component. When the total content of ascorbic acid-type antioxidant in terms of molar quantity is not less than 0.6 times the molar quantity of the carotenoid component, the total content of ascorbic acid-type antioxidant is sufficient for exerting an effect in terms of suppressing decomposition or loss of the carotenoid component. When the total content of ascorbic acid-type antioxidant in terms of molar quantity is not more than 7.0 times the molar quantity of the carotenoid component, a sufficient amount of carotenoid component can be contained.

The carotenoid-containing composition may contain an antioxidant other than those described above, such as butyl hydroxy toluene (BHT) or butyl hydroxy anisole (BHA).

[Other Components]

The carotenoid-containing composition may include, besides the components described above, other oil components usually employed as oil components.

Other oil components are not particularly limited as long as they are components that do not dissolve in an aqueous medium but dissolve in an oil medium, and those having properties and functions suitable for the purpose may appropriately be selected and used. Examples thereof include unsaturated fatty acids, fats and fatty oils such as coconut oil, fat-soluble vitamins such as tocopherol, and ubiquinones.

Examples of unsaturated fatty acids include a monounsaturated fatty acid (such as ω-9 or oleic acid) or polyunsaturated fatty acid (such as ω-3 or ω-6), each of which has 10 or more carbon atoms, preferably from 18 to 30 carbon atoms. Any known unsaturated fatty acid may be used, and examples of ω-3 fatty oils and ω-3 fats include linolenic acid, eicosapentaenoic acid (EPA) and docosahexaenoic acid (DHA), and fish oils containing such ω-3 fatty oils or fats.

Examples of ubiquinones include coenzymes Q such as coenxyme Q10.

Examples of fat-soluble vitamins include fat-soluble vitamins E, vitamins A, and vitamins D, and oil-solubilized derivatives of erythorbic acid. Of these, fat-soluble vitamins E, which have high antioxidative capacity and can be used as radial scavengers (antioxidants), are preferable.

Vitamins E are not particularly limited, and examples thereof include those selected from a group of compounds consisting of tocopherol and derivatives thereof, and a group of compounds consisting of tocotrienol and derivative thereof. These may be used singly, or in combination of two or more thereof. It is also possible to use a compound selected from the group of compounds consisting of tocopherol and derivatives thereof and a compound selected from the group of compounds consisting of tocotrienol and derivatives thereof, in combination.

The group of compounds consisting of tocopherol and derivatives thereof include dl-α-tocopherol, dl-β-tocopherol, dl-γ-tocopherol, dl-δ-tocopherol, dl-α-tocopherol acetate, dl-α-tocopherol nicotinate, dl-α-tocopherol linoleate and dl-α-tocopherol succinate. Of these, dl-α-tocopherol, dl-β-tocopherol, dl-γ-tocopherol and dl-δ-tocopherol, and mixtures thereof (mix tocopherol) are more preferable. Furthermore, preferable tocopherol derivatives include carboxylic acid esters of these tocopherols, especially acetic acid esters of these tocopherols.

The group of compounds consisting of tocotrienol and derivatives thereof include α-tocotrienol, β-tocotrienol, γ-tocotrienol and δ-tocotrienol. Furthermore, preferable tocotrienol derivatives include acetic esters of these tocotrienols.

Examples of vitamins A include retinol, 3-hydroretinol, retinal, 3-hydroretinal, retinoic acid, 3-dehydroretinoic acid and vitamin A acetate. Examples of vitamins D include vitamins $D_2$ to $D_7$ and other vitamins D. Examples of other fat-soluble vitamin substances include vitamin E nicotinate and other esters; and vitamins K such as vitamins $K_1$ to $K_3$.

Furthermore, examples of fat-soluble vitamins also include fatty acid esters of erythorbic acid such as erythorbyl palmitate and erythorbyl tetraisopalmitate; and fatty acid esters of vitamin $B_6$ such as pyridoxine dipalmitate, pyridoxine tripalmitate, pyridoxine dilaurate and pyridoxine dioctanoate.

Examples of fatty oils and fats other than those described above include fatty substances that are liquid at normal temperature (fatty oils) and fatty substances that are solid at normal temperature (fats).

Examples of the liquid fatty substances include olive oil, camellia oil, macadamia nut oil, castor oil, avocado oil, evening primrose oil, turtle oil, corn oil, mink oil, rapeseed oil, egg-yolk oil, sesame oil, persic oil, wheat germ oil, sasanqua oil, linseed oil, safflower oil, cotton seed oil, perilla oil, soybean soil, peanut oil, tea seed oil, kaya oil, rice bran oil, china wood oil, japanese tung oil, jojoba oil, bran oil, triglycerin, glycerin trioctanoate, glycerin triisopalmitate, salad oil, safflower oil, palm oil, coconut oil, peanut oil, almond oil, hazelnut oil, walnut oil, grape seed oil, squalene and squalane.

Examples of the solid fatty substances include beef tallow, hardened beef tallow, hoof oil, beef bone fat, mink oil, egg-yolk oil, lard, horse fat, mutton tallow, hardened oil, cacao fat, coconut oil, hardened coconut oil, palm oil, hardened palm oil, Japanese wax, Japanese wax kernel oil and hardened castor oil.

Of these, coconut oil that is a middle-chain fatty acid triglyceride is preferably used from the viewpoints of the particle diameter and stability of an emulsion composition.

In the invention, it is preferable that a compound (hereinafter collectively referred to as "tocopherol", as necessary) selected from the group consisting of tocopherol, tocotrienol, and derivatives thereof, which are included in fat-soluble vitamins, is contained together with other oil phase components with a view to improving properties in the composition.

When the tocopherol is used in combination with other oil phase components, the amount of tocopherol to be used is preferably from 5% by mass to 35% by mass, and more preferably from 7% by mass to 20% by mass, with respect to the total mass of oil components.

(Oil-in-Water Emulsion Composition)

As described above, the carotenoid-containing composition may be an oil-in-water emulsion composition containing an emulsifying agent, which is obtained by emulsification and mixing of the oil phase composition and the water phase composition, or a powder composition obtained by drying the oil-in-water emulsion composition.

In the case of an emulsion composition, the content of oil phase composition is preferably from 0.1% by mass to 50% by mass, more preferably from 0.5% by mass to 25% by mass, and further preferably from 0.2% by mass to 10% by mass, with respect to the total mass of the emulsion composition, from the viewpoint of exerting the functions of the oil components. In the case of a powder composition, the content of oil phase composition is preferably from 10% by mass to 50% by mass, more preferably from 10% by mass to 40% by mass, and further more preferably from 10% by mass to 30% by mass, with respect to the total mass of the powder composition.

The oil-in-water emulsion composition may include an emulsifying agent that is usable as an oil phase component, in addition to the components described above. Examples of emulsifying agents that can be used as oil phase components include emulsifying agents having HLB of 7 or lower and selected from those described below.

[Water Phase Composition]

The water phase composition is formed from an aqueous medium, especially water, and preferably contains at least an emulsifying agent.

The emulsifying agent may be any one of an anionic surfactant, a cationic surfactant, an amphoteric surfactant or a nonionic surfactant.

From the viewpoint of emulsification power, the emulsifying agent preferably has an HLB of 10 or more, and more preferably 12 or more. When the HLB of the emulsifying agent is too low, there are cases in which the emulsification power is insufficient. From the viewpoint of obtaining an anti-foaming effect, an emulsifying agent having an HLB of from 5 to less than 10 may also be used.

The HLB indicates a balance between hydrophilicity and hydrophobicity which is usually employed in the field of surfactants. A calculation formula usually used therefor, such as the Kawakami expression, may be used. The Kawakami expression is shown below.

$$HLB = 7 + 11.7 \log(M_w/M_O)$$

Here, $M_w$ represents the molecular weight of hydrophilic group(s), and $M_O$ represents the molecular weight of hydrophobic groups.

Numeral values of HLB described in catalogs, etc. may also be employed.

As is understood by the expression above, an emulsifying agent having any desired HLB value can be obtained utilizing the additive property of HLB.

A preferable content of the emulsifying agent in the oil-in-water emulsion composition or the powder composition generally varies with the form of the composition. In the case of an emulsion composition, the content of emulsifying agent is preferably from 0.5 to 30% by mass, more preferably from 1 to 20% by mass, and further more preferably from 2 to 15% by mass, with respect to the entire emulsion composition. In the case of a powder composition, the content of emulsifying agent is preferably from 0.1 to 50% by mass, more preferably form 5 to 45% by mass, and further more preferably from 10 to 30% by mass, with respect to the entire powder composition. When the content of emulsifying agent is within the above ranges, the surface tension between the oil phase and the poor solvent phase can easily be lowered, and problems such as severe foaming of the emulsion composition are prevented because the content of emulsifying agent is not excessive.

In each of the powder composition and the emulsion composition, the total mass of emulsifying agent may be within a range of from 0.1 to 10 times the total mass of oil components (including the carotenoid component). From the viewpoints of decreasing the sizes of dispersed particles and suppressing foaming, the total mass of emulsifying agent is preferably within a range of from 0.5 to 8 times the total mass of oil components (including the carotenoid component), and particularly preferably from 0.8 to 5 times the total mass of oil components (including the carotenoid component). When the total mass of emulsifying agent is within the above range, a favorable dispersion stability of the composition can be achieved. The scope of the "emulsifying agent" as used in the invention does not include the specific (poly)glycerin fatty acid ester described above Among emulsifying agents, nonionic surfactants are preferable due to low-irritating properties and low environmental influence thereof. Examples of nonionic surfactants include a sucrose fatty acid ester, a polyglycerin fatty acid ester, an organic acid monoglyceride, a propylene glycol fatty acid ester, a polyglycerin-condensed ricinoleic acid ester, a sorbitan fatty acid ester and a polyoxyethylene sorbitan fatty acid ester.

In the sucrose fatty acid ester, the number of carbon atoms in a fatty acid for forming the sucrose fatty acid ester is preferably from 12 to 20, and more preferably from 14 to 16, from the viewpoint of the stability of dispersed particles in the composition.

Preferable examples of sucrose fatty acid esters include sucrose dioleate, sucrose distearate, sucrose dipalmitate, sucrose dimyristate, sucrose dilaurate, sucrose monooleate, sucrose monostearate, sucrose monopalmitate, sucrose monomyristate and sucrose monolaurate. Of these, sucrose monooleate, sucrose monostearate, sucrose monopalmitate, sucrose monomyristate and sucrose monolaurate are particularly preferable.

In the invention, these sucrose fatty acid esters may be used singly, or in mixture of two or more thereof.

The carotenoid-containing composition contains the specific polyglycerin fatty acid ester described above. Independently from this, the water phase composition may contain a polyglycerin fatty acid ester (a second polyglycerin fatty acid ester) having an HLB of 10 or more.

Examples of the polyglycerin fatty acid ester (the second polyglycerin fatty acid ester) include an ester of a polyglycerin having an average polymerization degree of 2 or more, preferably an average polymerization degree of from 6 to 15, and more preferably an average polymerization degree of from 8 to 10, and a fatty acid having from 8 to 18 carbon atoms such as caprylic acid, capric acid, lauric acid, myristic acid, palmitic acid, stearic acid, oleic acid or linoleic acid.

Preferable examples of the polyglycerin fatty acid ester (the second polyglycerin fatty acid ester) include hexaglycerin monooleate, hexaglycerin monostearate, hexaglycerin monopalmitate, hexaglycerin monomyristate, hexaglycerin monolaurate, decaglycerin monooleate, decaglycerin monostearate, decaglycerin monopalmitate, decaglycerin monomyristate and decaglycerin monolaurate.

Of these, decaglycerin monooleate (HLB=12), decaglycerin monostearate (HLB=12), decaglycerin monopalmitate (HLB=13), decaglycerin monomyristate (HLB=14) and decaglycerin monolaurate (HLB=16) are more preferable.

These polyglycerin fatty acid esters may be used singly, or in mixture of two or more thereof.

In the invention, the sorbitan fatty acid ester is preferably a sorbitan fatty acid ester in which each fatty acid has preferably 8 or more carbon atoms, and more preferably 12 or more carbon atoms. Preferable examples of the sorbitan fatty acid ester include sorbitan monocaprylate, sorbitan monolaurate, sorbitan monostearate, sorbitan sesquistearate, sorbitan tristearate, sorbitan isostearate, sorbitan sesquiisostearate, sorbitan oleate, sorbitan sesquioleate and sorbitan trioleate.

In the invention, these sorbitan fatty acid esters may be used singly, or in mixture of two or more thereof.

As the polyoxyethylene sorbitan fatty acid ester, a polyoxyethylene sorbitan fatty acid ester in which each fatty acid has 8 or more carbon atoms, more preferably 12 or more carbon atoms, is preferable. The length (added molar number) of ethylene oxide of the polyoxyethylene is preferably from 2 to 100, and more preferably from 4 to 50.

Preferable examples of polyoxyethylene sorbitan fatty acid esters include polyoxyethylene sorbitan monocaprylate, polyoxyethylene sorbitan monolaurate, polyoxyethylene sorbitan monostearate, polyoxyethylene sorbitan sesquistearate, polyoxyethylene sorbitan tristearate, polyoxyethylene sorbitan isostearate, polyoxyethylene sorbitan sesquiisostearate, polyoxyethylene sorbitan oleate, polyoxyethylene sorbitan sesquioleate and polyoxyethylene sorbitan trioleate.

These polyoxyethylene sorbitan fatty acid esters may be used singly, or in mixture of two or more thereof.

Furthermore, a phospholipid such as lecithin may be contained as an emulsifying agent in the invention.

A phospholipid that can be used in the invention contains, as essential components, a glycerin skeleton, a fatty acid residue and a phosphoric acid residue, to which a base or a polyhydric alcohol is bonded; this phospholipid is also referred to as lecithin. Since the phospholipid has a hydrophilic group and a hydrophobic group in its molecule, it has been widely used as an emulsifying agent in the fields of foods, pharmaceuticals and cosmetics.

A lecithin product having a lecithin purity of 60% or higher is industrially used as lecithin, and may be used in the invention. From the viewpoints of formation of oil droplets having a fine particle diameter and stability of the functional oil component, those generally referred to as high purity lecithin are preferable, the lecithin purity of which is 80% or higher, more preferably 90% or higher.

Examples of phospholipids include various types of known phospholipids which are obtained by extraction/separation from plants, animals and microorganisms.

Specific examples of such phospholipids include various lecithins derived from plants such as soybean, corn, peanut, rapeseed and wheat, animals such as egg yolk and bovine, and microorganisms such as *Escherichia coli*.

Examples of chemical names of such lecithins include glycerolecithins such as phosphatidic acid, phosphatidyl glycerol, phosphatidyl inositol, phosphatidyl ethanolamine, phosphatidyl methyl ethanolamine, phosphatidyl choline, phosphatidyl serine, bisphosphatidic acid and diphosphatidyl glycerol (cardiolipin); and sphingolecithins such as sphingomyelin.

In the invention, lecithins that can be used include, in addition to the high purity lecithin, hydrogenated lecithin, enzymatically-decomposed lecithin, enzymatically-decomposed hydrogenated lecithin, hydroxylecithin, etc. These lecithins, which can be used in the invention, may be used singly, or in mixture of two or more thereof.

[Water-Soluble Encapsulating Agent]

When the carotenoid-containing composition is a powder composition obtained by drying an emulsion composition, the carotenoid-containing composition preferably contains a water-soluble encapsulating agent in order to protect the oil droplets during a powderization process at the time of drying or during storage of the powder. The inclusion of a water-soluble encapsulating agent allows fine particle diameters of the oil droplets to be maintained, and suppresses deterioration of the carotenoid component in the oil droplets.

The inclusion of a water-soluble encapsulating agent can provide excellent water dispersibility of the oil component when the powder composition is re-dissolved in water, and can provide excellent transparency of the carotenoid-containing composition after the re-dissolution.

The water-soluble encapsulating agent is preferably a polysaccharide (hereinafter simply referred to as "fructose polymer or oligomer") that is at least one selected from a fructose polymer and a fructose oligomer, each of which is composed of sugar units including at least two fructose units.

The fructose polymer or oligomer in the invention refers to a polymer or oligomer which contains fructose as a repeating unit and which is composed of sugar units formed by bonding between plural sugar units through dehydration condensation. In the invention, those having fewer than 20 sugar repeating units including fructose units are referred to as fructose oligomers, and those having 20 or more sugar repeating units are referred to as fructose polymers.

From the viewpoints of drying suitability and decrease in the size of oil droplets at the time of re-dissolution, the repeating number of sugar units is preferably from 2 to 60, and more preferably from 4 to 20. When the repeating number of sugar units (polymerization degree of fructose) is 2 or more, the moisture-absorption ability of the water-soluble encapsulating agent is not excessively strong, and, for example, a reduction in recovery ratio due to adhesion to a drying container during the drying process can effectively be prevented. When the repeating number of sugar units (polymerization degree of fructose) is 60 or fewer, an increase in the particle diameters of oil droplets at the time of re-dissolution of the powder composition in water can effectively be prevented.

The fructose polymer or oligomer may further contain monosaccharides, other than fructose, at a molecular terminal or in the molecular chain. Examples of other monosaccharide units that can be contained include, but are not limited to, glucose, galactose, mannose, idose, altrose, gulose, talose, allose, xylose, arabinose, lyxose, ribose, threose, erythrose, erythrulose, xylulose, ribulose, psicose, sorbose and tagatose. Of these monosaccharides, glucose is preferable from the viewpoint of easy availability. The linking position of other monosaccharide units is preferably at a terminal of a fructose chain from the viewpoint of attaining fine oil droplets when the powder composition is re-dissolved.

When the fructose polymer or oligomer contains saccharides other than fructose, the content ratio of other saccharides in terms of polymerization degree (the number of units) is 50% or lower, and more preferably 30% or lower, with respect to the number of fructose units, from the viewpoints of drying suitability and obtainment of fine oil droplets at the time of re-dissolution of the powder composition.

From the viewpoints of storage stability of a colorant and easy availability, the water-soluble encapsulating agent preferably used in the invention is, for example, inulin. In the invention, inulin refers to a fructose polymer or oligomer having one glucose at a terminal thereof. Inulin is known to widely exist in the nature, and large amounts thereof are contained in chicory, Jerusalem artichoke (Helianthus tuberosus), dahlia, garlic, Chinese chive, onion, etc. Details of inulin are described in Handbook of Hydrocolloids, G. O. Phillips, P. A. Williams Ed., 397-403, (2000) CRC Press. In general, a chain length is expressed by designating glucose unit as G and fructose unit as F. The scope of inulin in the invention does not include sucrose, which is expressed as GF.

Inulins extracted from nature are polymers or oligomers of GF2 (kestose), GF3 (nystose), and from GF4 (fructosylnystose) to about GF60, or mixtures thereof.

Inulin in the invention may be a commercial product obtained by hot-water separation and extraction from a root of chicory, Jerusalem artichoke, dahlia or the like, or by concentration of the obtained aqueous solution (extract), or by powderization through spray drying. Examples thereof include FRUTAFIT (manufactured by Sensus Corporation) extracted from a chicory root, BENEO (Orafti Corporation) extracted from a chicory root, a dahlia root-derived reagent (Wako Pure Chemical Industries Ltd., Sigma-Aldrich) and chicory root-derived reagent (Sigma-Aldrich).

The fructose oligomer and polymer in the invention may be one prepared from sucrose using the fructan transfer activity of β-fructofuranosidase. Examples thereof include FUJI FF (manufactured by Fuji Nihon Seito Corporation) and GF2 (manufactured by Meiji Seika Pharma Co., Ltd.).

In the inulin used in the invention, the repeating number (polymerization degree) of fructose is preferably from 2 to 60 from the viewpoints of obtaining fine oil droplets at the time of re-dissolution of the powder composition, and the polymerization degree of fructose is more preferably from 4 to 20 from the viewpoints of adhesion to an apparatus at the time of spray drying and solubility in water.

The fructose polymer or oligomer in the invention has preferably been added by the time of emulsification; however, it is also possible to add a portion or entire volume of the fructose polymer or oligomer after emulsification.

Besides the fructose polymer or oligomer, other water-soluble polymers or oligomers may also be used. Examples of other water-soluble polymers or oligomers include agarose, starch, carageenan, gelatin, xanthan gum, gellan gum, galactomannan, casein, tragacanth gum, xyloglucan, β-glucan, curdlan, water-soluble soybean fibers, chitosan, alginic acid and sodium alginate, but are not limited thereto.

The content (mass) of the water-soluble encapsulating agent in the carotenoid-containing composition is preferably from 0.5 times to 50 times the total mass of oil components in the carotenoid-containing composition, more preferably from 1 times to 20 times the total mass of oil components in the carotenoid-containing composition, further more preferably from 1 times to 10 times the total mass of oil components in the carotenoid-containing composition, and still more preferably from 2 times to 5 times the total mass of oil components in the carotenoid-containing composition, from the viewpoint of shape maintenance and solubility.

The water-soluble encapsulating agent may be contained in the water phase of the carotenoid-containing composition. The water-soluble encapsulating agent may be contained in the water phase composition at the time of the pressure emulsification described below. The water-soluble encapsulating agent may be added to the water phase of the carotenoid-containing composition after the pressure emulsification.

[Other Additive Components]

In addition to the components described above, components usually used in the field of foods or the like may be incorporated, as appropriate, into the carotenoid-containing composition in accordance with the form of the carotenoid-containing composition. The additive component may be incorporated as a component of the oil phase component mixture liquid, the carotenoid-containing oil phase composition or the water phase composition, or incorporated as an additive component for the water phase of the carotenoid-containing composition, depending on the properties of the additive component.

Examples of such other components include polyhydric alcohols such as glycerin and 1,3-butyleneglycol; monosaccharides and polysaccharides such as glucose, fructose, lactose, maltose, sucrose, pectin, κ-carageenan, locust bean gum, guar gum, hydroxypropyl guar gum, xanthan gum, karaya gum, tamarind seed polysaccharides, gum arabic, tragacanth gum, hyaluronic acid, sodium hyaluronate, sodium chondroitin sulfate and dextrin; sugar alcohols such as sorbitol, mannitol, maltitol, lactose, maltotriose and xylitol; inorganic salts such as sodium chloride and sodium sulfate; proteins having a molecular weight of higher than 5,000 such as casein, albumin, methylated collagen, hydrolyzed collagen, water-soluble collagen and gelatin; synthetic polymers such as a carboxyvinyl polymer, sodium polyacrylate, polyvinyl alcohol, polyethylene glycol and an ethylene oxide-propylene oxide block copolymer; water-soluble cellulose derivatives such as hydroxylethyl cellulose/methyl cellulose; flavonoids such as catechin, anthocyanin, flavone, isoflavone, flavan, flavanone and rutin; phenolic acids such as chlorogenic acid, ellagic acid, gallic acid and propyl gallic acid; lignans; curcumins; and coumarins. These components may be contained as, for example, a functional component, an excipient, a viscosity regulator or a radical scavenger, based on the functions thereof.

Furthermore, other additives which are usually used for the application of interest, such as various medicinal components, pH adjusters, pH buffers, ultraviolet absorbers, antiseptics, flavors and colorants, may also be used.

(Method of Producing Fat-Reducing Agent)

The fat-reducing agent of the invention can be obtained by a production method including: preparing an oil phase component mixture liquid containing the carotenoid component and the (poly)glycerin fatty acid ester (referred to as oil phase component mixture liquid preparation process); and heating the oil phase mixture liquid at a temperature equal to or higher than the melting temperature of the carotenoid component (referred to as oil phase component heating process).

According to this production method, since the oil phase component mixture liquid is heated at a temperature equal to or higher than the melting temperature of the non-crystalline carotenoid component, re-crystallization of the crystalline carotenoid in the carotenoid component can be suppressed, and a carotenoid-containing composition in which the non-crystalline state is stably maintained can be obtained. Thus, according to the present production method, a fat-reducing agent containing the carotenoid-containing composition as an active ingredient can efficiently be obtained.

In the oil phase component mixture liquid preparation process, oil phase components, including the carotenoid component and the (poly)glycerin fatty acid ester, are mixed so as to obtain an oil phase mixture liquid. There is no particular limitation on the mixing of the oil phase components.

In the oil phase component heating process, the oil phase component mixture liquid is heated at a temperature equal to or higher than the melting temperature of the carotenoid component. It is necessary that the temperature for heating the oil phase component mixture liquid be a temperature equal to or higher than the melting temperature of the carotenoid component. If the heating temperature is lower than the melting temperature of the carotenoid component, the crystalline carotenoid does not dissolve, and, therefore, a large amount of crystals are left in the carotenoid-containing composition. In the oil phase component heating process, since the crystalline carotenoid co-dissolves with the (poly)glycerin fatty acid ester, the crystals thereof can be dissolved at lower temperatures.

The melting temperature of the carotenoid component means a temperature at which the crystalline carotenoid in the carotenoid component dissolves. In a case in which the carotenoid component is formed only from the crystalline carotenoid, the melting temperature of the carotenoid component means the melting temperature of the crystalline carotenoid. In a case in which the carotenoid component includes components other than the crystalline carotenoid, the melting temperature of the carotenoid means a temperature at which carotenoid in the carotenoid component dissolves.

For example, in a case in which a carotenoid-containing oil derived from a natural product is used as the carotenoid component, impurities etc., are sometimes contained, in which case it is known that the crystalline carotenoid in the carotenoid component dissolves at a temperature lower than the melting temperature of the crystalline carotenoid. In this case, the temperature at which the crystalline carotenoid in the carotenoid component dissolves corresponds to the "melting temperature of the carotenoid component" in the invention.

The melting temperature of carotenoid component can be confirmed by a method generally used for confirming a melting temperature, and can be confirmed, for example, by DSC.

Specifically, the heating temperature (co-dissolution temperature) employed in the oil phase component heating process may vary with the type or the like of the crystalline carotenoid or carotenoid component to be used. In general, in the case of a lycopene-containing carotenoid component, the heating temperature may be set to a temperature of from 150° C. to 200° C., and from the viewpoint of suppression of heat decomposition, the heating temperature is preferably from 150° C. to 180° C., and more preferably from 150° C. to 170° C.

From the viewpoint of suppressing decomposition of the crystalline carotenoid, the highest heating temperature applied in the oil phase component heating process is preferably a temperature that is within 10° C. from the melting temperature of the carotenoid component (i.e., the difference between the highest temperature in the heat treatment and the melting temperature of the carotenoid component is 10° C. or smaller), and more preferably a temperature such that the difference between the highest temperature in the heat treatment and the melting temperature of the carotenoid component is very small, for example, 5° C. or smaller.

The heating time employed in the oil phase component heating process may be any period of time with which the carotenoid component in the oil phase component mixture liquid dissolves. The heating time is preferably from 10 minutes to 60 minutes, and more preferably from 15 minutes to 45 minutes, from the viewpoints of efficiently converting the crystals to a non-crystal state and suppressing decomposition of the crystalline carotenoid caused by excess heat. However, the heating time is not limited to the above ranges.

It is important that the entire oil phase component mixture liquid in the oil phase component heating process has a uniform temperature. Therefore, the oil phase component mixture liquid is preferably sufficiently stirred while heating. It is desirable to heat the oil phase component mixture liquid at a constant temperature while stirring, using a hermetically sealed container.

Through the oil phase component heating process, a carotenoid-containing composition as an oil phase composition is obtained.

The method of producing a fat-reducing agent is preferably any one of the following embodiments from the viewpoint of more reliably suppressing the decomposition or loss of the crystalline carotenoid during the production process:

(1) a production method including: mixing the carotenoid component containing the crystalline carotenoid and the (poly)glycerin fatty acid ester to obtain an oil phase component mixture liquid; and heating the oil phase component mixture liquid for from 15 minutes to 45 minutes under temperature conditions in which the highest temperature is equal to or higher than the melting temperature of the carotenoid component and in which the difference between the highest temperature and the melting temperature of the carotenoid component is 10° C. or smaller;

(2) a production method including: mixing the carotenoid component containing lycopene and the (poly)glycerin fatty acid ester to obtain an oil phase component mixture liquid; and heating the oil phase component mixture liquid at a temperature of from 150° C. to 170° C.;

(3) a production method including: mixing the carotenoid component containing lycopene, the (poly)glycerin fatty acid ester, and an ascorbic acid-type antioxidant that is at least one selected from the group consisting of ascorbic acid and an ascorbic acid ester, to obtain an oil phase component mixture liquid; and heating the oil phase component mixture liquid at a temperature of from 150° C. to 170° C.

In the preferable embodiments listed above, it is more preferable that the carotenoid component, the (poly)glycerin fatty acid ester and the ascorbic acid-type antioxidant, which form the oil phase component mixture liquid, are the same as the carotenoid component, the (poly)glycerin fatty acid ester and the ascorbic acid-type antioxidant that are used in preferable embodiments of the carotenoid-containing composition described above.

(Method of Producing Emulsion Composition)

In a case in which the carotenoid-containing composition is an emulsion composition, the production method may further include, after the oil phase component heating process, emulsifying the oil phase composition obtained through the oil phase component heating process and a water phase composition containing water phase components including an emulsifying agent (emulsification process).

In this way, an oil-in-water emulsion composition in which the oil phase component containing the carotenoid component is finely dispersed as oil droplets (emulsified particles) in water can be obtained. In the emulsion composition, the carotenoid component containing the crystalline carotenoid is stably retained.

The ratio (by mass) between the oil phase and the water phase in the emulsification is not particularly limited. The oil phase/water phase ratio (mass %) is preferably from 0.1/99.9 to 50/50, more preferably from 0.5/99.5 to 30/70, and further more preferably from 1/99 to 20/80.

An oil phase/water phase ratio of 0.1/99.9 or higher is preferable since such an oil phase/water phase ratio results in a tendency that the content of active ingredient is not low, and that practical problems of the emulsion composition do not occur. An oil phase/water phase proportion of 50/50 or lower is preferable since such an oil phase/water phase ratio results in a tendency that the concentration of the emulsifying agent is not low, and that the emulsion stability of the emulsion composition does not deteriorate.

The emulsification may be carried out by a one-step emulsification operation. However, it is preferable to carry out emulsification operation having two or more steps, from the viewpoint of obtaining fine and uniform emulsified particles.

Specifically, it is particularly preferable to use two or more emulsification apparatuses, such as a method including carrying out a one-step emulsification operation in which emulsification is carried out using a usual emulsification apparatus utilizing shear action (such as a stirrer or an impeller stirrer, a homomixer or a continuous flow shear apparatus) and further carrying out emulsification using, for example, a high-pressure homogenizer. Use of a high-pressure homogenizer allows the emulsion to contain fine liquid droplets having more uniform particle diameters. Furthermore, in order to obtain liquid droplets having further uniform particle diameters, the emulsification as described above may be repeated plural times.

Any generally-known emulsification methods may be used as an emulsification means employed for the emulsification, and examples thereof include spontaneous emulsification, surface chemical emulsification, electric emulsification, capillary emulsification, mechanical emulsification and ultrasonic emulsification.

Surface chemical emulsification methods such as a PIT emulsification method or a gel emulsification method are known, and are useful methods for decreasing the sizes of emulsified particles. This method has an advantage in that only a small amount of energy is consumed, and this method is suitable for finely emulsifying materials that are vulnerable to thermal deterioration.

Methods using a mechanical force, specifically, methods in which oil droplets are divided by applying a strong shear force from the outside, are used as versatile emulsification methods. A most general method among the methods using a mechanical force is use of a high-speed high-shear agitator. Examples of the agitator include a homomixer, a disper mixer, and an ultramixer, which are commercially-available.

Another example of mechanical emulsification apparatuses useful for decreasing the droplet sizes is a high-pressure homogenizer, and various apparatuses are commercially available. Since high-pressure homogenizers are capable of applying a larger shear force than stirring methods, the droplet sizes can be decreased even when the amount of emulsifying agent is relatively small.

High-pressure homogenizers are roughly classified into chamber-type high-pressure homogenizers having a fixed orifice, and homogenizing valve high-pressure homogenizers in which the aperture of the orifice can be adjusted.

Examples of chamber high-pressure homogenizers include MICROFLUIDIZER (manufactured by Microfluidics Co., Ltd.), NANOMIZER (manufactured by Yoshida Kikai Co., Ltd.) and ULTIMIZER (Sumino Machine Limited).

Examples of homogenizing valve high-pressure homogenizers include Gaulin-type homogenizers (manufactured by APV), Lanier-type homogenizers (manufacture by Lanier Corporation), high-pressure homogenizers (manufactured by Niro Soavi), homogenizers (manufactured by Sanwa Engineering Ltd.), high-pressure homogenizers (manufactured by Izumi Food Machinery Co., Ltd.) and ultrahigh-pressure homogenizers (manufactured by IKA Japan K.K.).

Ultrasonic homogenizers are dispersion apparatuses which have relatively high energy efficiency and which are emulsification apparatuses having simple structures. Examples of high-power ultrasonic homogenizers that can be used for manufacturing include ultrasonic homogenizers US-600, US-1200T, RUS-1200T, MUS-1200T, etc. (all manufactured by NihonSeiki Kaisha Ltd.), and ultrasonic processors UIP2000, UIP-4000, UIP-8000 and UIP-16000 (all manufactured by Hielscher Ultrasonic GMBH). These high-power ultrasonic application apparatuses are used at a frequency of 25 kHz or less, preferably at a frequency from 15 kHz to 20 kHz.

Examples of other known emulsification means include methods using a static mixer, a microchannel, a micromixer, a membrane emulsification apparatus or the like, each of which does not have a stirring unit connected to the outside and requires only a small energy. These methods are also useful.

The temperature conditions for the emulsification and dispersion in the invention are not particularly limited. However, the temperature is preferably from 10 to 100° C. from the viewpoint of the stability of functional oil components, and a preferable range may be selected, as appropriate, in accordance with the melting temperature of the functional oil components to be used.

In a case in which a high-pressure homogenizer is used in the invention, the treatment is preferably carried out at a pressure of 50 MPa or higher, more preferably from 50 MPa to 280 MPa, and further more preferably from 100 MPa to 280 MPa.

From the viewpoint of maintaining the particle diameter of dispersed particles, it is preferable to cool the emulsion liquid, which is an emulsified/dispersed composition, using some cooling apparatus immediately after passing the chamber, specifically within 30 seconds from passing the chamber, and preferably within 3 seconds from passing the chamber.

The production method may include drying the oil-in-water emulsion composition obtained through the emulsification process, to obtain a powder composition (hereinafter sometimes referred to as "powderization process"). As a result of this process, a fat-reducing agent is obtained as a powder composition. The fat-reducing agent as a powder composition has storage stability since it is in the powder form. Further, crystallization of the crystalline carotenoid in the composition is suppressed when the composition is in the state of a powder composition as well as when the composition is in the state of an emulsion composition obtained by re-dissolving the powder composition in an aqueous medium.

Known drying means may be used as a drying means for use in the powderization process, and examples thereof include natural drying, heat drying, hot-air drying, high-frequency drying, ultrasonic drying, reduced-pressure drying, vacuum drying, freeze drying and spray drying. These means may be used singly, or in combination of two or more thereof.

In the invention, since functional materials relatively weak to heat are often contained, reduced-pressure drying, vacuum drying, freeze drying or spray drying is preferable. Furthermore, a method in which vacuum (reduced-pressure) drying is carried out while a temperature of from the freezing temperature to 0° C. is maintained, which is one method of vacuum drying, is also preferable.

When carrying out vacuum drying or reduced-pressure drying, it is preferable that drying is carried out by repeating concentration while the degree of vacuum is gradually increased, so as to avoid scattering caused by bumping.

In the invention, freeze drying, in which moisture is removed by sublimating ice from a material in the frozen state, is preferable. The freeze drying method has significant advantages in that, since the drying process generally proceeds at a temperature of 0° C. or lower, generally at a temperature of from about −20° C. to −50° C., thermal deterioration of the material does not occur, and taste, color, nutritional values, shape, texture, etc. can easily be returned, by rehydration, to those before the drying.

Examples of commercially-available freeze dryers include, but are not limited to: a freeze dry apparatus VD-800F (manufactured by TAITEC Corporation), FLEXIDRY MP (manufactured by FTS Systems Corporation), DURATOP DURA STOP (manufactured by FTS Systems Corporation), Takara freeze dryer type A (manufactured by Takara ATM), laptop freeze dryer FD-1000 (manufactured by Tokyo Rikakikai Co., Ltd.), vacuum freeze dryer FD-550 (manufactured by Tokyo Rikakikai Co., Ltd.) and a vacuum freeze dryer (manufactured by Takara Seisakujo).

In the invention, a spray drying method is particularly preferable as the drying means from the viewpoints of attaining both of production efficiency and quality. Spray drying is one type of convection hot-air drying. A liquid composition is sprayed into hot air as fine particles of several hundred micrometers or less, and the fine particles fall in the reaction tower while being dried, whereby the fine particles are collected as solid powder. Although the material is temporarily exposed to hot air, since the temperature does not significantly increase owing to the exposure time being extremely short and the latent heat of vaporization of water, the thermal deterioration of the material hardly occurs as in the case of freeze drying, and changes due to rehydration is also small. In the case of using a material that is extremely weak to heat, cold air may be supplied instead of hot air. Although supply of cold air provides lower drying capacity, supply of cold air is preferable since it realizes milder drying.

Examples of commercially-available spray dryers include, but are not limited to, spray dryer SD-1000 (manufactured by Tokyo Rikakikai Co., Ltd.), spray dryer L-8i (manufactured by Ohkawara Kakohki Co., Ltd.), closed spray dryer CL-12 (manufactured by Ohkawara Kakohki Co., Ltd.), spray dryer ADL310 (manufactured by Yamato Scientific Co., Ltd.), minispray dryer B-290 (manufactured by Nihon Buchi K.K.), PJ-MiniMax (manufactured by Powdering Japan) and PHARMASD (manufactured by Niro).

Furthermore, it is preferable to carry out shaping into a granular shape, which provides excellent handleability, simultaneously with drying, using an apparatus capable of simultaneously carrying out drying and granulation such as a fluidized bed granulation drying apparatus MP-01 (manufactured by Powrex Corporation) or a built-in fluidized bed spray dryer FSD (manufactured by Niro).

The average particle diameter in the oil-in-water emulsion composition or in the powder composition obtained by powderization refers to the particle diameter of dispersed particles (oil droplets) in the emulsion composition in the case of the oil-in-water emulsion composition, and refers to the particle diameter of dispersed particles (oil droplets) obtained when a 1% by mass aqueous solution is prepared from the powder composition (re-dissolution) in the case of the powder composition.

The particle diameter of the dispersed particles may be measured using a commercially-available particle size distribution analyzer or the like. Known methods for measuring a particle size distribution in an emulsion include optical microscopy, confocal laser microscopy, electron microscopy, atomic force microscopy, a static light scattering method, laser diffraction, a dynamic light scattering method, centrifugal sedimentation, electrical pulse measurement, chromatography, an ultrasonic attenuation method, etc., and apparatuses utilizing the respective principles are commercially available From the viewpoint of particle diameter range and ease of measurement in the invention, a dynamic light scattering method is preferable for the measurement of the particle diameter of dispersed particles in the invention. Examples of commercially-available measurement apparatuses employing dynamic light scattering include NANOTRAC UPA (manufactured by Nikkiso Co., Ltd.), a dynamic light scattering particle size distribution analyzer LB-550 (manufactured by Horiba) and a concentrated-system particle diameter analyzer FPAR-1000 (manufactured by Otsuka Electronics Co., Ltd.). In the invention, a value measured at 25° C. using a particle diameter analyzer FPAR-1000 (manufactured by Otsuka Electronics Co., Ltd.) is used as the particle diameter.

In other words, for measuring the particle diameter, the composition is diluted 20-fold with pure water in the case of the oil-in-water emulsion composition, or diluted with pure water to have a solid content concentration of 1% by mass in the case of the powder composition, and a median diameter (d=50) measured using a particle diameter analyzer FPAR-1000 (manufactured by Otsuka Electronics Co., Ltd.) is employed as the particle diameter (average particle diameter).

The particle diameter of the emulsified particles may be controlled by adjusting factors such as the stirring conditions (such as shear force, temperature, pressure) of the production method or the ratio between the oil phase and the water phase, as well as by adjusting the components of the composition.

The particle diameter in the oil-in-water emulsion composition is preferably from 50 nm to 300 nm from the viewpoint of transparency and the viewpoint of absorptivity, and, from the viewpoint of transparency, the particle diameter in the oil-in-water emulsion composition is more preferably from 50 nm to 200 nm, and most preferably from 50 nm to 150 nm.

(Fat-Reducing Agent)

The fat-reducing agent of the invention contains the carotenoid-containing composition as an active ingredient. The fat-reducing agent may be formed from only the carotenoid-containing composition, or may further contain a pharmaceutically acceptable carrier suitable for the dosage form of the fat-reducing agent, in addition to the carotenoid-containing composition.

The fat-reducing agent of the invention may have an appropriate form in accordance with the carotenoid-containing composition contained therein. For example, the fat-reducing agent may be in the form of an oil phase composition or in the form of an emulsion composition, or may once be made in the form of an oil phase composition or an emulsion composition and then changed into an appropriate form suitable for the desired dosage form. The form applicable to the fat-reducing agent may be any of liquid, solid, powder or gel, and examples thereof include a solution, a pill, a hard capsule, a soft capsule and a granule.

The effective amount of the carotenoid-containing composition in the fat-reducing agent may vary with the dosage form or administration mode of the fat-reducing agent. When the fat-reducing agent is a composition in the form of a liquid or an emulsion (including those obtained by re-dispersing powder in water), the effective amount may be set to be from 99% by mass to 0.0001% by mass, preferably from 90% by mass to 0.0005% by mass, with respect to the total mass of the composition. When the fat-reducing agent is a composition in the solid form, the effective amount of the carotenoid-containing composition may be set to be from 95% by mass to 0.0001% by mass, preferably from 90% by mass to 0.0001% by mass, with respect to the total mass of the composition. However, the effective amount is not particularly limited. The dosage amount may be set to a therapeutically effective amount. Although the dosage amount may vary with the dosage form or the like, the dosage amount may generally be set to be from 0.001 mg to 10,000 mg per 1 kg of body weight per day, preferably from 0.005 mg to 5,000 mg per 1 kg of body weight per day, and more preferably from 0.01 mg to 1,500 mg per 1 kg of body weight per day, in terms of the amount of carotenoid component.

Although the administration mode of the fat-reducing agent is preferably oral administration, parenteral administration such as transrectal administration or sublingual administration may be applied.

Since the fat-reducing agent of the invention can exert an effect in terms of easy and effective suppression of accumulation of fat, especially neutral fat, the fat-reducing agent can preferably be used in foods. In other words, the invention provides a food containing the fat-reducing agent.

The food according to the invention may be any food containing the fat-reducing agent, and specifics of the fat-reducing agent are directly applicable to the food of the invention.

The content of the fat-reducing agent in the food of the invention may be any content within a range in which an effect in terms of reducing the accumulation amount of fat can be obtained. The amount of the fat-reducing agent contained as an active ingredient in the food may be, for example, 0.001% by mass or more with respect to the total mass of the food.

Furthermore, examples of the food include general foods such as energy drinks, revitalizers, non-alcoholic drinks and frozen desserts, as well as dietary supplements in the form of pills, granules or capsules.

In a case in which the food of the invention is used as a functional food, the amount of the powder composition of the invention to be added cannot be generally specified because it may vary with the type or purpose of the product. However, the powder composition may be added to have a content in the range of from 0.01 to 10% by mass, preferably from 0.05 to 5% by mass, with respect to the product. When the addition amount is 0.01% by mass or more, desired effects may be exerted, and when the addition amount is 10% by mass or less, suitable effects are often exerted with high efficiency.

The scope of the invention includes application of the fat-reducing agent to prevention or treatment of a symptom or disease that is accompanied by an increase in fat accumulation amount. In other words, the scope of the invention includes a method of preventing or treating a symptom or disease accompanied by fat accumulation, the method including administering the fat-reducing agent to a subject that exhibits a symptom potentially involving an increase in fat accumulation amount or a subject with a disease potentially involving an increase in fat accumulation amount. The specifics of the fat-reducing agent described above are directly applicable to the fat-reducing agent applicable to the method of preventing or treating. According to the present method of preventing or treating, fat accumulation can easily be suppressed, and amelioration of the symptom or disease accompanied by fat accumulation may be achieved.

Examples of symptoms or diseases accompanied by an increase in fat accumulation amount include hyperlipidemia, obesity, life-style related diseases, hypertension, arteriosclerosis, diabetes, cardiac infarction and cerebral infarction.

The scope of "reduction in fat accumulation amount" includes a reduction of, or suppression of an increase of, the amount of fat (especially neutral fat) which is, or can be, accumulated in the body, such as in the blood, under the skin or in internal organs after administration of the fat-reducing agent, as compared to before the administration of the fat-reducing agent.

With respect to the components, contents, production methods, administration doses, etc. for an anti-cerebral atrophy agent of the invention, the specifics of the fat-reducing agent of the invention can be directly applied.

As described above, the carotenoid-containing composition of the invention can be used in the production of a fat-reducing agent. The invention also provides a method of producing a pharmaceutical agent for reducing fat, in which the carotenoid-containing composition described above is used. Details of the pharmaceutical agent for reducing fat are the same as the details of the fat-reducing agent described above.

EXAMPLES

Hereinbelow, the invention is described by referring to examples. However, the invention is not limited thereto. In the following description, amounts expressed using "part(s)" or "%" are based on mass, unless specified otherwise.

Example 1

(1) Preparation of Oil Phase Composition

The oil phase components described below (except mix tocopherol) were conditioned, from room temperature, to have a temperature in a range of from 160° C. to 165° C., and stirred for dissolution for 20 minutes while heating, thereby obtaining a carotenoid-containing oil phase composition. The obtained carotenoid-containing oil phase composition was conditioned to have a temperature of 60° C. and maintained at that temperature, and mix tocopherol was added thereto while stirring, as a result of which an oil phase composition 1 was obtained.

(2) Preparation of Water Phase Composition

The water phase components described below were mixed and stirred for dissolution while being heated at 70° C., and were then subjected to coarse dispersion for 90 seconds using a 600 W ultrasonic homogenizer (US-150T, manufactured by NihonSeiki Kaisha Ltd.), thereby obtaining a water phase composition 1.

[Oil Phase Composition 1]

| Lycopene paste (lycopene concentration: 18%) | 8.9 g |
| Diglyceryl monostearate | 0.9 g |
| 50% solution of calcium ascorbate | 7.1 g |
| Mix tocopherol | 1.3 g |

[Water Phase Composition 1]

| Sucrose laurate | 11.1 g |
| Lecithin | 1.8 g |
| Inulin | 25.6 g |
| Water | 246.9 g |

Here, LYCOPENE 18 (manufactured by Kyowa Wellness Co., Ltd.) was used as the lycopene paste, NIKKOL DGMS (HLB=5.0, manufactured by Nikko Chemicals Co., Ltd.) was used as the diglyceryl monostearate, RIKEN E OIL 800 (manufactured by Riken Vitamin Co., Ltd.) was used as the mix tocopherol, RYOTO SUGAR ESTER L-1695 (HLB=16, manufactured by Mitsubishikagaku Foods Corporation) was used as the sucrose laurate, LECION P (manufactured by Riken Vitamin Co., Ltd.) was used as the lecithin, and FUJI FF (manufactured by Fuji Nihon Seito Corporation) was used as the inulin. The melting temperature of LYCOPENE 18 was 153° C. (endothermic peak measured by DSC). The content (molar quantity) of calcium ascorbate corresponds to 3.06 times the molar quantity of the carotenoid component.

(3) Preparation of Emulsion

The oil phase composition 1 was maintained at 60° C. while being stirred, and the water phase composition 1 produced as described above and maintained at 70° C. was added thereto. The resultant mixture was dispersed for 3 minutes using a 600 W ultrasonic homogenizer, thereby obtaining a coarsely-dispersed emulsion 1 (lycopene concentration: 0.53%).

Subsequently, the coarsely-dispersed emulsion 1 was subjected to high-pressure emulsification treatment four times using a STAR BUSRT MINI (manufactured by Sugino Machine Limited) at a pressure of 245 MPa and a temperature of 30° C., thereby obtaining an emulsion 1.

Then, the obtained emulsion 1 was spray-dried by spray drying (using a spray drier ADL310 (manufactured by Yamato Scientific Co., Ltd.)) under conditions of a spray pressure of 0.15 MPa, an exit temperature of 80° C. and a throughput of 7 ml/minute, and the resultant powder was collected using a cyclone, thereby obtaining a powder composition 1 having a lycopene concentration of 3%.

Examples 2 to 5 and Comparative Examples 1 and 2

Oil phase compositions 2 to 5 and 7 to 8 and water phase compositions 2 to 5 and 7 to 8 were obtained in the same manner as in Example 1, except that the types and contents of the oil phase components and the water phase components were changed as shown in Table 1. Emulsification was carried out in the same manner as in Example 1, using the oil phase compositions 2 to 5 and 7 to 8 and the water phase compositions 2 to 5 and 7 to 8, thereby obtaining emulsions 2 to 5 and 7 to 8, respectively. Furthermore, spray drying was performed, thereby obtaining powder compositions 2 to 5 and 7 to 8.

In Table 1, COCONARD MT (HLB=1, manufactured by Kao Corporation) was used as the glyceryl tri(caprylate-caproate), HEXAGLYN 5-SV (the number of glycerin units=7, the number of stearate chains=5, manufactured by Nikko Chemicals Co., Ltd.) was used as the hexaglycerol pentastearate, Ascorbic acid PM (manufactured by Showa Denko K.K.) was used as the magnesium ascorbyl phosphate, and DECAGLYN 1-SV (the number of glycerin unites=10, the number of stearate chains=1, HLB=12.0, manufactured by Nikko Chemicals Co., Ltd.) was used as the decaglyceryl monostearate.

Example 6

An emulsion 6 was obtained by performing the preparation and emulsification of the compositions for the respective phases in the same manner as in Example 1, except that the types and contents of the oil phase components and the water phase components were changed as shown in Table 1, and that the spray drying was not performed.

In Table 1, MGS-F50V (the number of glycerin units=1, the number of stearate chains=1, manufactured by Nikko Chemicals Co., Ltd., HLB=3.5) was used as the glyceryl monostearate, DECAGLYN 1-L (the number of glycerin units=10, the number of laurate chains=1, HLB=15.5, manufactured by Nikko Chemicals Co., Ltd.) was used as the decaglyceryl monolaurate, and the glycerin used was a product of Kao Corporation.

Comparative Example 3

A powder composition 9 was obtained by performing the preparation, emulsification and spray drying of the compositions for the respective phases in the same manner as in Example 1, except that the types and contents of the oil phase components and the water phase components were changed as shown in Table 1, and that the oil phase composition was prepared only by mixing the oil phase components without heating.

Comparative Example 4

A powder composition 10 was obtained by performing the preparation, emulsification and spray drying of the compositions for the respective phases in the same manner as in Example 1, except that the heating treatment for preparing the oil phase composition was performed at 70° C. for 30 minutes.

(b) Evaluation of Crystals by Polarization Microscopic Observation

The emulsion/powder composition was visually observed using a PCLIPSE LV100POL (manufactured by Nikon Corporation). In the observation of the emulsion, the emulsion was observed as it was. In the observation of the powder composition, the powder composition was observed after the powder composition was dispersed in water to form an emulsion having a solid concentration of 1%. The evaluation of the results of the visual observation was carried out as described

TABLE 1

| | | Example 1 | Example 2 | Example 3 | Example 4 | Example 5 | Example 6 | Comparative Example 1 | Comparative Example 2 | Comparative Example 3 | Comparative Example 4 |
|---|---|---|---|---|---|---|---|---|---|---|---|
| Oil Phase | Lycopene paste (lycopene content: 18%) (g) | 8.9 | 5.9 | 8.9 | 8.9 | 8.9 | 8.9 | 8.9 | 8.9 | 8.9 | 8.9 |
| | Diglyceryl monostearate (g) | 0.9 | 0.6 | | 0.9 | 0.9 | | 0.0 | 0.0 | 0.0 | 0.9 |
| | Hexaglyceryl pentastearate (g) | | | 0.9 | | | | | | | |
| | Glyceryl monostearate (g) | | | | | | 0.9 | | | | |
| | Decaglyceryl monolaurate (g) | | | | | | | | 0.9 | | |
| | Glyceryl tri(caprylate-caproate) (g) | | 2.9 | | | | 4.7 | 0.9 | | 0.9 | |
| | Calcium ascorbate (g) | 3.5 | 2.3 | 3.5 | 0.0 | | 7.1 | 3.5 | 3.5 | 0.0 | 3.5 |
| | Magnesium ascorbyl phosphate (g) | | | | | 7.1 | | | | | |
| | Mix tocopherol (g) | 1.3 | 0.9 | 1.3 | 1.3 | 1.3 | 1.3 | 1.3 | 1.3 | 1.3 | 1.3 |
| Water phase | Pure water (g) | 246.9 | 244.4 | 246.9 | 246.9 | 246.9 | 246.9 | 246.9 | 246.9 | 246.9 | 246.9 |
| | Sucrose laurate (g) | 11.1 | 37.0 | 11.1 | 11.1 | 11.1 | 12.8 | 11.1 | 11.1 | 6.1 | 11.1 |
| | Decaglyceryl laurate (g) | | | | | | 4.3 | | | 2.0 | |
| | Lecithin (g) | 1.8 | 6.0 | 1.8 | 1.8 | 1.8 | 2.8 | 1.8 | 1.8 | 1.8 | 1.8 |
| | Inulin (g) | 25.6 | 0.0 | 25.6 | 29.1 | 22.0 | 0.0 | 25.6 | 25.6 | 32.1 | 25.6 |
| | Glycerin (g) | | | | | | 10.3 | | | | |
| | Lycopene concentration (emulsion) | 0.53% | 0.35% | 0.53% | 0.53% | 0.53% | 0.53% | 0.5% | 0.5% | 0.5% | 0.53% |
| | Lycopene concentration (powder) | 3.0% | 2.00% | 3.0% | 3.0% | 3.0% | — | 3.0% | 3.0% | 3.0% | 3.0% |
| | Antioxidant/lycopene (ratio by mol) | 1.51 | 1.49 | 1.50 | 0.00 | 4.13 | 3.05 | 1.51 | 1.50 | 0.00 | 1.51 |

[Evaluation]

[1] Evaluation of Properties of Powder Composition and Emulsion

The evaluation of the emulsions before the drying process and the obtained powder products were carried out as described below. Furthermore, evaluation was also carried out as Comparative Example 5 with respect to a case in which only LYCOPENE 18 was used. Table 2 shows the evaluation results.

(a) DSC Endothermic Peak Temperature

The endothermic temperature and the exothermic temperature were determined using a DSC Q2000 (TA Instruments Japan) by carrying out one temperature increase-decrease (15° C./min) cycle within a temperature range of from 30° C. to 200° C. In the case of measuring the emulsion, the measurement was carried out after the emulsion was freeze-dried for removing water. In the case of measuring the powder composition, the composition was measured in the powder state.

below. Here, the ranks A to C indicate that at least 90% by mass of the crystalline carotenoid is in the non-crystalline state.

Evaluation by Visual Observation

A: Hardly any lycopene-derived crystals were observed.

B: Lycopene-derived crystals were slightly observed.

C: Lycopene-derived crystals were diffusely present, but the quantity thereof is small.

D: Lycopene-derived crystals were present all over the observed image.

(c) Average Particle Diameter

The average particle diameter of the dispersed particles in the emulsion formed from the water phase components and oil phase components was obtained as d=50 diameter at 25° C. as measured using a particle diameter analyzer FPARE-1000 (manufactured by Otsuka Electronics Co., Ltd.). In the case of the emulsion, the measurement was carried out after the emulsion was diluted 20-fold by adding pure water to the emulsion. In the case of the powder composition, the measurement was carried out after an emulsion having a solid concentration of 1% was prepared by adding pure water to the powder composition.

(d) Residual Lycopene Ratio

From among the emulsions and powder composition of Examples 1 and 3 to 6 and Comparative Examples 1 to 4, each of the emulsions was diluted 1,062-fold with acetone and sufficiently dissolved therein to have a lycopene concentration of 0.005 vol. %, and, from each of the powder compositions, an emulsion was formed and then diluted 5.65-fold by adding pure water, and sufficiently dissolved, and then further diluted 1,062-fold with acetone and sufficiently dissolved, so that the resultant solution similarly had a lycopene concentration of 0.005 vol. %. Subsequently, filtration using a 0.45 μm filter was carried out, and absorbance at the maximum and a supernatant thereof was collected. The collected supernatant was dried and solidified, and thereafter re-dissolved in chloroform/methanol=1/1 (v/v), and the content of lycopene was obtained using HPLC.

The relationship between the length of time from the administration to the blood sampling and the lycopene concentration in the blood plasma was graphically illustrated, and the area under the curve (AUC, the area below the concentration in blood–time curve) with respect to the period from the administration to 8 hours after the administration was obtained for each of the administered compositions, and used as the dynamic absorption value. Table 2 shows the results. A larger dynamic absorption value is evaluated as indicating a higher active ingredient concentration in blood.

TABLE 2

| | Example 1 | Example 2 | Example 3 | Example 4 | Example 5 | Example 6 | Comparative Example 1 | Comparative Example 2 | Comparative Example 3 | Comparative Example 4 | Comparative Example 5 |
|---|---|---|---|---|---|---|---|---|---|---|---|
| DSC absorption peak temperature | None | None | None | None | None | None | 153° C. | 154° C. | 153° C. | 154° C. | 153° C. |
| Polarization microscopic observation | A | A | B | A | A | A | D | D | D | D | D |
| Average particle diameter (nm) Emulsion | 125 | 212 | 120 | 121 | 123 | 52 | 113 | 122 | 148 | 1 μm≤ | — |
| Powder composition | 140 | — | 131 | 129 | 138 | — | 121 | 136 | 175 | 1 μm≤ | — |
| Lycopene residual ratio | 96% | 98% | 97% | 30% | 92% | 99% | 97% | 99% | 99% | 100% | — |
| AUC (ng * 8 h/ml) | 5390 | 8730 | — | — | — | — | — | — | 830 | — | 540 | peak wavelength (from 465 nm to 475 nm) of the filtrate was measured using a spectrophotometer V-630 (manufactured by JASCO Corporation).

In the case of Example 2, the residual ratio was measured in the same manner as in Examples 1 and 3 to 6 and Comparative Examples 1 to 4, except that, in order to set the lycopene concentration to 0.005 vol. %, the emulsion was diluted 708-fold with acetone, and, from the powder composition, an emulsion was formed and then diluted 5.65-fold by adding pure water, and sufficiently dissolved, and then further diluted 708-fold with acetone and sufficiently dissolved.

LYCOPENE 18 was diluted with acetone to a lycopene concentration of 0.005 vol. %, and the absorbance at a peak wavelength was similarly measured. For evaluation, assuming that the obtained absorbance of this lycopene is 100%, the residual ratio of each composition was obtained as a ratio thereto.

(e) Dynamic Absorption

Each of the emulsions or powder composition of Examples 1 to 6 and Comparative Examples 1 to 5 (in the case of Comparative Example 5, a diluted product of which the lycopene concentration was adjusted to 2 mg/ml by using COCONARD MT) was diluted to have a lycopene concentration of 2 mg/ml, and was orally administered in an administration volume of 10 ml/kg to non-fasted 6-week-old male rats (n=4 for each group). Then, 0.4 ml of blood was sampled at 1, 2, 3, 4, 6, 8 and 24 hours after the administration.

Each blood sample was subjected to centrifugation, and a supernatant blood plasma was collected in an amount of 0.1 ml. The blood plasma was dissolved in acetone, and then hexane was added thereto, and the sample was left to stand As is understood from Tables 1 and 2, the carotenoid-containing compositions of Examples 1 to 6, of which the oil phase compositions were prepared by thermally treating LYCOPENE 18 together with a polyglycerin fatty acid ester containing 1 to 6 glycerin units and 1 to 5 fatty acid units at a temperature higher than the melting temperature of LYCOPENE 18, exhibited no DSC endothermic peak, and were composition in which crystallization was suppressed, regardless of whether the carotenoid-containing composition was in the form of an emulsion or in the form of powder. Table 2 shows only the results obtained using the compositions in the form of emulsions.

From the results of the experiments of administration to rats, it is clear that each of the carotenoid-containing compositions of Examples 1 to 6 exhibits excellent lycopene absorption, and is a carotenoid-containing composition exhibiting high absorptivity in which crystallization of lycopene is suppressed.

[2] Fat Accumulation Evaluation 1

The powder composition 1 of Example 1 and the oil phase composition that was obtained during the preparation of the powder composition 1 were evaluated for the effect with respect to suppression of fat accumulation in the following manner.

Five-week-old male Sprague Dawley (registered name) rats (SD rats) (CLEA Japan, Inc., Shizuoka, Japan) were purchased, and quarantined and acclimated for one week. Thereafter, the rats were randomly grouped, each group consisting of 8 rats. Lycopene powder and a lycopene crystal solution were dissolved in water for injection (Otsuka Pharmaceutical Co., Ltd., Tokyo, Japan), and were intragastrically administered by forced oral administration using a metal gastric tube in doses, in terms of lycopene masses, of 0.25 mg/kg, 1.25 mg/kg and 6.25 mg/kg. The administration was repeatedly carried out once a day for 4 weeks, and the rats were fasted for 16 hours from the evening of the final day of the administration, and the blood was sampled. Thereafter, the rats were euthanized by exsanguination. Neutral fat amounts were measured using the obtained blood.

To the control group, only the lycopene paste (Comparative Example 5) or the water for injection was administered in the same manner as in the administration of the powder composition 1 and oil phase composition of Example 1, and the blood was sampled, and the neutral fat amounts were thereafter measured.

Table 3 shows the results. As shown in Table 3, a decrease in neutral fat in the blood was confirmed in the groups in which the lycopene powder composition or oil phase composition of the Example was administered.

TABLE 3

| Type | Administration dose (mg/kg) | Neutral fat amount in blood (mg/dl) |
|---|---|---|
| Lycopene-containing composition | | |
| Powder composition | 0.25 | 38.02 ± 13.87 |
| | 1.25 | 32.38 ± 17.29 |
| | 6.25 | 29.75 ± 15.46 |
| Oil phase composition | 0.25 | 43.36 ± 18.26 |
| | 1.25 | 37.14 ± 15.89 |
| | 6.25 | 33.17 ± 14.89 |
| Lycopene paste | 6.25 | 44.19 ± 21.03 |
| Only the water for injection | — | 47.88 ± 23.01 |

[3] Fat Accumulation Evaluation 2

The powder composition 1 of Example 1 and the oil phase composition that was obtained during the preparation of the powder composition 1 were evaluated for the effect with respect to suppression of fat accumulation in a case in which rats were fed with a high-fat diet, in the following manner.

Five-week-old male Sprague Dawley (registered name) rats (SD rats) (CLEA Japan, Inc., Shizuoka, Japan) were purchased, and quarantined and acclimated for one week. Thereafter, the rats were randomly grouped, each group consisting of 8 rats. Feeding for the groups, except one group, was switched to a high-fat diet.

A lycopene paste-dissolved solution, lycopene powder and a lycopene crystal solution were dissolved in water for injection (Otsuka Pharmaceutical Co., Ltd., Tokyo, Japan), and were intragastrically administered by forced oral administration using a metal gastric tube in doses, in terms of a lycopene mass, of 6.25 mg/kg. The administration was repeatedly carried out once a day for 4 weeks, and the rats were fasted for 16 hours from the evening of the final day of the administration, and the blood was sampled. Thereafter, the rats were euthanized by exsanguination. Then, internal organs were harvested, and the weight of the internal organs was measured. The obtained blood was used for measurement.

For the control group, only the lycopene paste (Comparative Example 5) was administered to the rats in the same manner as in the administration of the powder composition 1 and oil phase composition of Example 1, and the blood was sampled, and the neutral fat amounts were measured.

Table 4 shows the results.

TABLE 4

| Type | Neutral fat amount in blood (mg/dl) | Body weight (g) |
|---|---|---|
| Lycopene-containing composition | | |
| Powder composition | 35.88 ± 11.26 | 384.0 ± 21.4 |
| Oil phase composition | 40.19 ± 15.33 | 388.2 ± 25.6 |
| Lycopene paste | 51.00 ± 17.11 | 378.8 ± 27.7 |
| Only the water for injection (high-fat diet) | 52.25 ± 22.76 | 411.0 ± 23.8 |
| Only the water for injection (normal diet) | 47.88 ± 23.01 | 355.4 ± 19.0 |

As shown in Table 4, the body weights of rats in the control group, in which lycopene was not administered, were increased by feeding with a high-fat diet. In contrast, an increase in the body weights was suppressed in the groups in which the lycopene powder composition and the oil phase composition, respectively, were administered (Example 1) and in the group in which the lycopene paste was administered (Comparative Example 5).

Further, as shown in Table 4, a decrease in neutral fat amount in the blood was confirmed in the group in which the lycopene powder composition or the oil phase composition of the Example was administered. Ingestion of the composition of the Example resulted in a lower fat content in the blood than that in the case of ingestion of a high-fat diet as well as that in the case of ingestion of a normal diet. In contrast, the group administered with the lycopene paste exhibited hardly any decrease in the neutral fat amount in the blood, and it was clarified that a satisfactory effect in terms of suppressing neutral fat accumulation was not attained.

Furthermore, the group fed with a high-fat diet exhibited significantly inferior T-CHO, BUN, ALP and TG values in the blood than the group fed with a normal diet. However, deterioration of these values was not observed in the groups to which the lycopene powder composition and the oil phase composition, respectively, were administered (although data are not shown).

Therefore, according to the invention, a fat-reducing agent can be provided which contains a crystalline carotenoid and which has an effect in terms of reducing the accumulation amount of fat.

Japanese Patent Application No. 2011-072918 filed Mar. 29, 2011 is incorporated herein by reference in its entirety.

All publications, patent applications and technical standards mentioned in this specification are herein incorporated by reference to the same extent as if such individual publication, patent application or technical standard was specifically and individually indicated to be incorporated by reference.

The invention claimed is:

1. A method of reducing fat in a subject, comprising administering a fat-reducing agent to the subject, wherein the fat-reducing agent comprises a lycopene-containing composition as an active ingredient, the lycopene-containing composition including:
   a lycopene component including at least one crystalline lycopene, wherein at least 90% by mass of the crystalline lycopene is in a non-crystalline state; and
   a (poly)glycerin fatty acid ester, which is diglyceryl monostearate, wherein a dosage amount of the fat-reducing agent is set to be from 0.25 mg to 6.25 mg per 1 kg of body weight per day in terms of an amount of the lycopene component.

2. The method of reducing fat in a subject according to claim 1, wherein the total mass of the (poly)glycerin fatty acid ester is from 0.01 times to 10 times the total mass of the crystalline lycopene.

3. The method of reducing fat in a subject according to claim 1, wherein the fat-reducing agent further comprises an antioxidant.

4. The method of reducing fat in a subject according to claim 3, wherein the antioxidant comprises at least one selected from the group consisting of ascorbic acid, an ascorbic acid ester and salts thereof, in a molar quantity that is from 0.01 times to 10 times the molar quantity of the lycopene component.

5. The method of reducing fat in a subject according to claim 1, wherein the fat-reducing agent further comprises an emulsifying agent.

6. The method of reducing fat in a subject according to claim 5, wherein the emulsifying agent comprises a nonionic surfactant selected from the group consisting of a sucrose fatty acid ester, a polyglycerin fatty acid ester, an organic acid monoglyceride, a propylene glycol fatty acid ester, a polyglycerin-condensed ricinoleic acid ester, a sorbitan fatty acid ester and a polyoxyethylene sorbitan fatty acid ester.

7. The method of reducing fat in a subject according to claim 5, wherein the lycopene-containing composition is an oil-in-water composition in which an oil phase composition containing the lycopene component and the (poly)glycerin fatty acid ester is dispersed in a water phase composition containing water and the emulsifying agent.

8. The method of reducing fat in a subject according to claim 5, wherein the lycopene-containing composition is a powder composition obtained by drying an oil-in-water composition in which an oil phase composition containing the lycopene component and the (poly)glycerin fatty acid ester is dispersed in a water phase composition containing water and the emulsifying agent.

9. The method of reducing fat in a subject according to claim 1, wherein the lycopene-containing composition further includes at least one selected from the group consisting of ascorbic acid, an ascorbic acid ester and salts thereof as an antioxidant, in a molar quantity that is from 0.01 times to 10 times the molar quantity of the lycopene component.

10. A method of reducing fat in a subject according to claim 1, wherein the fat-reducing agent further comprises a polysaccharide that is at least one selected from the group consisting of a fructose polymer and a fructose oligomer, each of which is composed of sugar units including at least two fructose units.

11. A method of reducing fat in a subject according to claim 10, wherein the polysaccharide is inulin.

\* \* \* \* \*